(12) United States Patent
Seppälä

(10) Patent No.: US 6,948,495 B2
(45) Date of Patent: Sep. 27, 2005

(54) POWDER INHALER

(75) Inventor: Kari Seppälä, Helsinki (FI)

(73) Assignee: Orion Corporation, Espoo (FI)

( * ) Notice: Subject to any disclaimer, the term of this patent is extended or adjusted under 35 U.S.C. 154(b) by 181 days.

(21) Appl. No.: 10/240,782

(22) PCT Filed: Apr. 5, 2001

(86) PCT No.: PCT/FI01/00335

§ 371 (c)(1), (2), (4) Date: Jun. 13, 2003

(87) PCT Pub. No.: WO01/76668

PCT Pub. Date: Oct. 18, 2001

(65) Prior Publication Data

US 2004/0025874 A1 Feb. 12, 2004

(30) Foreign Application Priority Data

Apr. 6, 2000 (FI) .............................. 2000810

(51) Int. Cl.$^7$ .................... A61M 15/00; A61M 11/00
(52) U.S. Cl. ..................... 128/203.15; 128/200.23; 128/203.19
(58) Field of Search ............ 128/203.15, 200.17, 128/203.21, 203.19, 200.12, 200.18, 200.21, 200.22, 200.23

(56) References Cited

U.S. PATENT DOCUMENTS

| | | | |
|---|---|---|---|
| 3,789,843 A | * | 2/1974 | Armstrong et al. .... 128/200.23 |
| 3,900,138 A | * | 8/1975 | Phillips ....................... 222/340 |
| 4,668,231 A | * | 5/1987 | de Vries et al. ......... 604/891.1 |
| 5,069,204 A | * | 12/1991 | Smith et al. ............ 128/200.23 |
| 5,263,475 A | | 11/1993 | Altermatt et al. |
| 5,355,873 A | * | 10/1994 | Del Bon et al. ........ 128/200.23 |
| 5,437,270 A | | 8/1995 | Braithwaite |
| 5,447,151 A | * | 9/1995 | Bruna et al. ............ 128/203.15 |
| 5,549,101 A | * | 8/1996 | Trofast et al. ......... 128/203.15 |
| 5,840,279 A | | 11/1998 | Narodylo et al. |
| 5,857,457 A | | 1/1999 | Hyppola |
| 6,012,454 A | * | 1/2000 | Hodson et al. ........ 128/203.15 |
| 6,071,498 A | * | 6/2000 | Narodylo et al. ............ 424/46 |
| 6,354,290 B1 | * | 3/2002 | Howlett ................. 128/200.23 |
| 6,382,461 B1 | * | 5/2002 | Olsson .......................... 222/1 |
| 6,553,987 B1 | * | 4/2003 | Davies ................. 128/200.14 |
| 2003/0000524 A1 | * | 1/2003 | Anderson et al. ...... 128/203.23 |

FOREIGN PATENT DOCUMENTS

| | | |
|---|---|---|
| DE | 43 19 514 | 12/1994 |
| WO | WO 92/09322 | 6/1992 |
| WO | WO 93/03782 | 3/1993 |

* cited by examiner

*Primary Examiner*—Henry Bennett
*Assistant Examiner*—Shumaya B. Ali
(74) *Attorney, Agent, or Firm*—Finnegan, Henderson, Farabow, Garrett & Dunner, LLP

(57) ABSTRACT

An inhaler device comprising a container for powdered medicament, an inhalation channel, a movable metering member, a depressible actuator and a multiple dosage preventing means for locking the depressible actuator after use such that the actuator is unlocked only upon inhalation. The inhaler device is useful in the treatment of respiratory diseases such as asthma. The multiple dosage preventing means of the device eliminates the risk of unintentional overdosing.

8 Claims, 5 Drawing Sheets

POWDER INHALER

This application is a national stage filing of PCT International Application No. PCT/FI01/00335, filed on Apr. 5, 2001. This application also claims the benefit of priority under 35 U.S.C. § 119(a) to Finnish patent application ser. no. 20000810, filed on Apr. 6, 2000.

BACKGROUND OF THE INVENTION

The present invention relates to a device for dispensing of a powdered drug preparation by inhalation. The device is in particular a multiple-dose device without propellant gas, equipped with a means for preparing a dose to be inhaled and a means for preventing overdosing. The device of the invention is useful, for example, in the treatment of asthma.

The administering of a powdered drug preparation by inhalation from an inhaler is known. Multidose type powder inhalers comprising a drug container and a metering member for measuring and dispensing a unit dose are also known, for example from patent publications GB 2165159, EP 79478, and EP 166294. In these devices, a series of dosing recesses are notched into the surface of a cylindrical metering member. When the metering member is rotated, e.g. by pressing an actuation member, the dosing recesses will move first to a position in alignment with the powder container for being filled and thereafter to a position in alignment with the inhalation channel, whereupon an unit dose will fall by gravity from the dosing recess into the inhalation channel. Thereafter the dose of medicament is inhaled from the inhalation channel. These devices have the drawback that they make overdosing of the medicament possible by allowing the user to actuate the device repeatedly, whereby plurality of doses are dispensed into the inhalation channel. The user may then inadvertently draw a multiple dose by one inhalation.

Attempts have been made to solve the above-mentioned problem by using dispensing systems in which the dosing recess will not be emptied into the inhalation channel by gravity but, instead, the dose of medicament is inhaled directly from the dosing recess, such recesses having been notched into the surface of a metering member having the shape of a cylinder, a cone or a truncated cone, as disclosed in patent publications WO 92/00771 and WO 92/09322. However, the possibility of overdosing is not entirely eliminated, since repeated actuation of the device by the user is still possible. Overdosing is possible e.g. if the device is shaken between repeated actuations.

Recently, arrangements have been described to prevent unintentional multiple metering operations.

Thus, in the powder inhaler described in U.S. Pat No. 5,263,475, when an actuator (a push-button) is depressed, a spring biased slider slides into a groove and locks the push-button in depressed position. The lock can be released by pushing the slider manually back to its initial position.

More complex designs have also been described where the inhalation force is used to release the lock of the metering member. Since repeated actuation of the device without inhalation is not possible, it is ensured that only one dose at a time is dispensed from the inhalation channel to the lungs of the patient.

Thus, the powder inhaler shown in U.S. Pat. No. 5,447, 151 comprises a locking rod. When the device is actuated by depressing a pusher, air is compressed in a chamber and the compressed air pushes the locking rod against the horizontal wall of the pusher. When the pusher is released, a valve arrangement maintains the air pressure in the chamber such that when the pusher is in its rest position, the compressed air pushes the locking rod into a corresponding hole in the horizontal wall of the pusher. The pusher is then locked in its rest position and can not be operated. Inhalation through the inhalation channel causes the chamber to come into balance with atmospheric pressure, whereby the locking rod returns from the locking position to its rest position.

WO 97/00703 describes a powder inhaler comprising an actuating button connected to a metering lever that moves a metering member between filling and dispensing positions and a valve flap. When the actuating button is depressed, the metering lever moves the metering member to the dispensing position. A lug of the metering lever engages with a recess of the valve flap shaft, thereby locking the metering member to the dispensing position. The sucking in of air for inhalation is sufficient to rotate the valve flap and release the metering lever again.

WO 94/11044, WO 97/20589 and WO 99/38555 describe powder inhalers where the movement of the metering member from the filling position to the inhalation position is completed by the inhalation force of the user. Thus, a powdered dose enters the inhalation channel only when sufficient inhalation intensity is produced.

The powder inhaler described in WO 94/28957 is actuated by first pulling and then pushing a metering slide. If the actuating procedure is not followed by subsequent inhalation, a fresh metering operation is prevented by a hook like connection between an air throttle disposed in the inhalation channel and a spring incorporated into the top of the dosing slide. Upon inhalation the air throttle in the inhalation channel is opened and the hook connection undone for next metering operation.

Finally, in a powder inhaler described in WO 93/03782 the dose is inhaled while keeping the metering element button depressed. A sphere positioned in a channel which is inclined in the gravitational force direction, is used as a blocking member. The metering element has a finger that extends through a hole into the area of the blocking sphere. In its rest position the sphere blocks the metering operation. If the air stream is strong enough, the sphere moves in the channel thus allowing the metering operation by permitting the entry of the finger in the channel. This design requires the user to coordinate the actuation and inhalation steps when using the device.

The above arrangements for preventing unintentional multiple metering operations are structurally complex or require a close coordination between the metering operation and the inhalation by the patient. Therefore, there is a need for an improved powder inhaler eliminating the risk of unintentional overdosing.

SUMMARY OF THE INVENTION

The object of the present invention is an inhaler device which avoids the above mentioned disadvantages. The structure is simple and reliable, can be operated with one hand and does not require close coordination between the metering operation and the inhalation by the patient. Unintentional multiple metering operations are effectively prevented.

This is achieved by providing a manually actuatable inhaler allowing actuation before inhalation by the user comprising a container for powdered medicament: an inhalation channel through which air is drawn via a mouthpiece;

a movable metering member for metering a dose of powder in a first position, and for transferring the metered dose of powder into the inhalation channel in a second position;

a depressible actuator for the displacement of the metering member between the first and the second position;

a multiple dosage preventing means for locking the depressible actuator after it has been used such that the actuator is unlocked only upon inhalation comprising a projection communicating with the actuator, a passage in which the projection moves when the actuator is depressed, and a blocking element which, after the device has been actuated, by means of gravitational force moves to a position where it blocks the passage, and which by means of a inhalation force moves to a position where it opens the passage.

The metering of the medicament dose by the movable metering member can be constructed in number of ways.

In a preferred embodiment of the invention the movable metering member is in the form of a rotatable metering drum or disc equipped with one or more peripheral dosing recesses to receive in the first position a dose of medicament from the powder container and to bring in the second position the medicament into the inhalation channel. Such metering members have been described in e.g. WO 92/00771 and WO 92/09322.

Alternatively, the movable metering member can be in the form of a longitudinally movable metering rod or strip equipped with a dosing recess. Such metering member have been described e.g. in U.S. Pat. No. 5,447,151, U.S. Pat. No. 5,263,475 and EP 758911.

The displacement of the metering member between the first and the second positions by means of the depressible actuator can also be achieved in number of ways.

In a preferred embodiment of the invention the depressible actuator is in the form of a depressible device cover as disclosed in e.g. WO 92/09322. In this simple construction the cover has an elongation which engages with the teeth of the metering drum. Every time the device cover is depressed the engagement of the elongation with the teeth causes the metering drum to rotate.

Alternatively the depressible actuator may be a separated member protruding from the device cover as shown in WO 92/00771. It is also possible that the metering member is directly operable by the user in which case the metering member is also the actuator.

The depressible actuator is preferably biased to return to its rest position after the depressing force has been removed.

The device of the invention comprises a multiple dosage preventing means which eliminates the risk of unintentional overdosing. The multiple dosage preventing means of the device locks the depressible actuator after the actuator has been operated. The user can not again depress the actuator for metering another dose of medicament. The actuator is unlocked only if the user inhales through the device, whereby the dose is discharged from the inhalation channel and transferred into the pulmonary system of the user.

The multiple dosage preventing means consists of a projection communicating with the actuator a passage in which the projection moves when the actuator is depressed, and a blocking element. The term "communicate" means herein communicating or being connected either directly or indirectly via another element. Preferably the projection extends from the body of the depressible actuator. The position of the blocking element in relation to the passage determines whether the actuator is locked or not. When the blocking element enters the passage of the projection (into a blocking position), the movement of the projection in the passage is prevented, and thus the actuator can not be depressed. When the blocking element is removed from the passage (into a non-blocking position), the movement of the projection through the passage is allowed and thus the actuator is again depressible.

The blocking element is suitably mounted into the inhalation channel or into a separate channel which is in a fluid communication with the inhalation channel, such that the blocking element is able to move from the blocking position to the non-blocking position in response to the pressure change in the inhalation channel caused by the inhalation.

The transfer of the blocking element from the non-blocking position to the blocking position is caused by the gravitational force.

In one preferred embodiment of the invention the blocking element is in the form of a sphere freely movable along a loop-like channel which is in a fluid communication with the inhalation channel.

In another preferred embodiment the blocking element is in the form of a flap pivotally mounted into a channel which is in a fluid connection with the inhalation channel.

In the preferred embodiment of the invention the blocking element has three stationary positions. Preferably the blocking element has a first non-blocking position, into which the blocking element moves upon inhaling, a second non-blocking position, into which the blocking element moves when the actuator is again depressed, and a blocking position into which the blocking element moves when the depressible actuator is subsequently released.

In its first non-blocking position the blocking element is urged by the gravitational force to move towards the blocking position but is however maintained in its first non-blocking position by a blocking element releasing arm. The arm is suitably connected to the actuator such that pressing down the actuator causes the arm to release the blocking element, whereby the blocking element is transferred by the gravitational force to its second non-blocking position. In its second non-blocking position the blocking element is still urged by the gravitational force to move towards the blocking position but is however maintained in its second non-blocking position by the projection communicating with the actuator. The blocking element is maintained in its second non-blocking position as long as the actuator is being depressed, as the blocking element leans against the projection. As soon as the user no longer depresses the actuator i.e. releases the actuator, the return of the actuator back to its rest position causes the blocking element to be transferred to is blocking position by the gravitational force.

The device of the invention allows separate actuation and inhalation steps, i.e. the device allows the actuation step to be performed before the inhalation step. In particular, the device allows the user to actuate the device without simultaneous or preceding inhalation through the device. Thus the user is not required to closely coordinate the actuation and inhalation steps.

DETAILED DESCRIPTION OF THE INVENTION

The device of the invention is further illustrated below by way of examples with reference to FIGS. 1 to 9, wherein the device or parts thereof are depicted as transparent.

Figure 1:
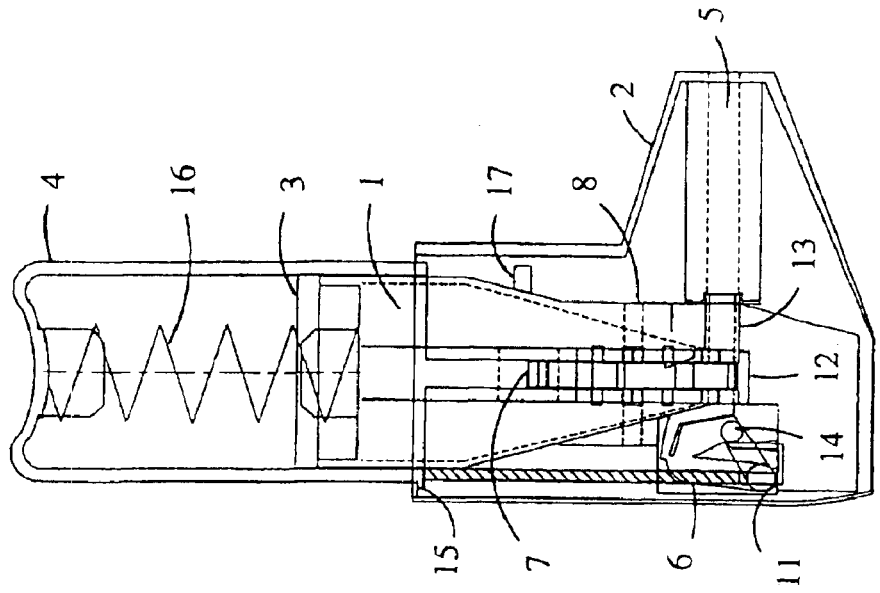
FIG. 1 is a side view of the inhaler device.

A side view of the inhaler device of the invention is shown in FIG. 1. The device has a medicament container (1) for a certain supply of powdered medicament, an inhalation channel (5), a rotatable metering disc (7) and a mouth piece (2). A lid (3) closes the upper edge of the medicament container (1). The cover (4) is adapted to cover the medicament container (1) and the lid (3). The wall of the container (1) has an elongate slot into which a vertically positioned metering disc (7) is rotatably secured by means of a disc axis (8) crossing the medicament container (1). The dimensions of the elongate slot correspond exactly with the shape of the metering disc (7) such that the metering disc (7) is in sliding contact with the sides of the slot thereby preventing the flow of powder through the slot. A multiple dosage preventing means (6,11,14), the structure and function of which will be explained later is shown on the left at the level of the inhalation channel (5).

Figure 2:
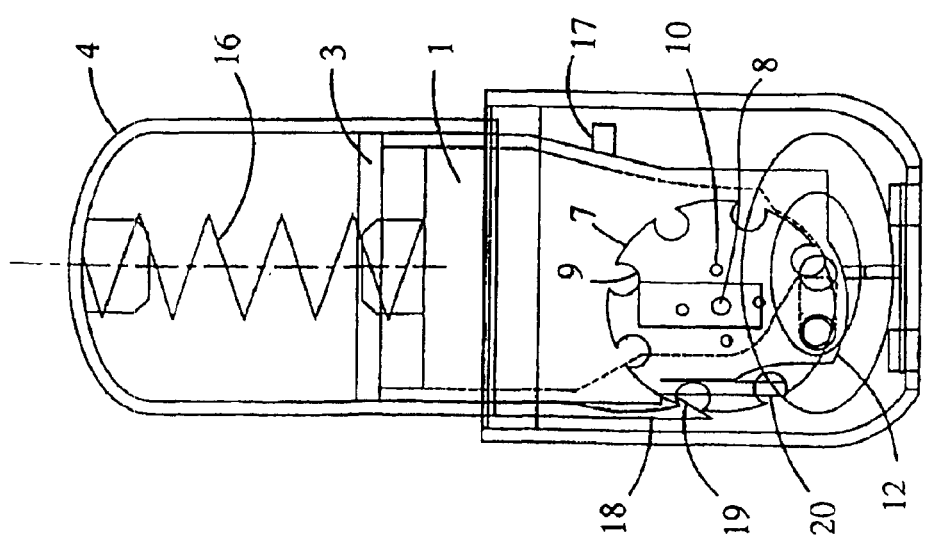
FIG. 2 is a front view of the inhaler device of FIG. 1.

The structure of the metering disc (7) can be best seen in FIG. 2 which shows a front view of the device. For the sake of better comprehension, the multiple dosage preventing means is not shown in FIG. 2. The metering disc (7) has several dosing grooves (9) located on the peripheral surface of the metering disc (7) and extending axially through the metering disc (7). The metering disc (7) extends into the interior of the container (1) such that some dosing grooves (9) are inside and others outside the container (1). When the metering disc (7) is rotated clockwise around the axis (8) each dosing groove (9) is transferred from outside to inside the container (1) and vice versa.

Turning again to FIG. 1, the inhalation channel (5) comprises, in the vicinity of the metering disc (7), a conduit in the form of an open cylindrical element (13) projecting from the vertical guide walls of the elongate slot. The cylindrical element (13) is provided with an opening for receiving a peripheral portion of the metering disc (7). When the metering disc (7) is rotated, it slides across the conduit formed by the cylindrical element (13). The cylindrical element (13), which has an inner diameter corresponding to the diameter of the dosing groove (9) is positioned at the level of the annular wall segment (12) so that the dosing groove (9) can be brought in register with the cylindrical element (13). When the dosing groove (9) is in register with the cylindrical element (13), the dosing groove (9) and the cylindrical element (13) form together a continuous tube-like channel, which determines the central part of the inhalation channel (5). Thereby substantially all air inhaled through the mouth piece (2) is conducted through the dosing groove (9).

The device has a depressible cover (4) serving as an actuator of the device. The depressible cover (4) is attached to the lower body by snapfastening means e.g. such as a peripheral lip (15) which puts an upward limit on the movement of the cover (4). The cover (4) is urged upwards by a spring (16) bearing firstly against the cover (4) and secondly against the lid (3).

The downward limit on the movement of the cover (4) is put by the edge (17) of the container (1). The cover (4) is provided with a driving member (18) for the stepwise rotation of the metering disc (7). The lower end of the driving member has a tooth-like projection (19) for engagement with the edge of a dosing groove (9) of the metering disc (7).

The device is actuated by depressing the cover (4), whereby the driving member (18), having some flexibility in the direction of the side wall of the device, moves down until the tooth-like projection (19) is engaged with a dosing groove (9). The detent nose (20) extending from the vertical guide wall also engages into a dosing groove (9) such that analogue to a ratchet rotation is only possible to one direction.

When the cover (4) is released, the cover (4) and the driving member (18) are urged upwards by the action of the spring (16). Thereby the tooth-like projection (19) of the driving member (18) causes the metering disc (7) rotate so that rotation can only be accomplished stepwise corresponding to the peripheral distance between the dosing grooves (9). The cylindrical element (13) forming part of the inhalation channel and the detent nose (20) are positioned such that the driving member (18) automatically aligns one dosing groove (9) with the cylindrical element (13) forming part of the inhalation channel.

The multiple dosage preventing means for locking the depressible actuator after use such that the actuator is unlocked only upon inhalation comprises a longitudinal rod-like projection (6) extending downwards from the vertical rear wall of the cover (4), a passage (11) in which the projection (6) moves when the cover (4) is depressed, and a blocking element in the form of a sphere (14). The structure of the multiple dosage preventing means is shown in FIGS. 3–6, which are now referred to.

Figure 5:
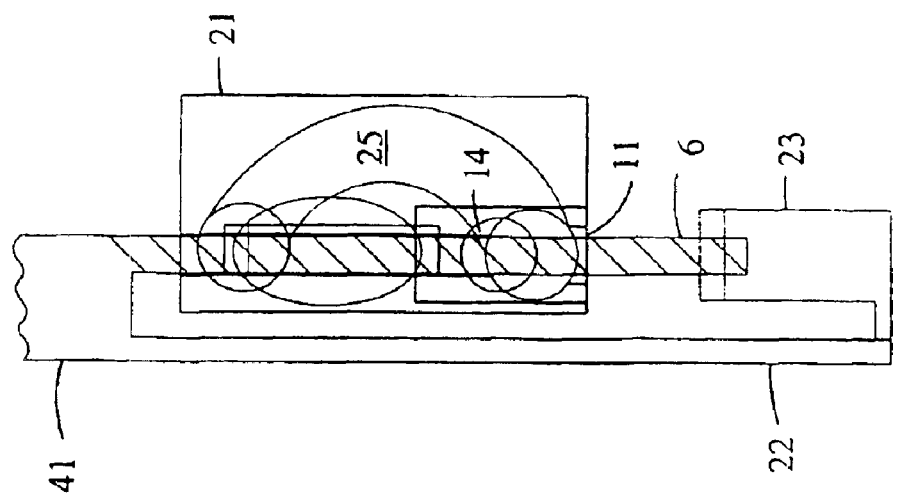
FIG. 5 is a back view of the device of FIG. 4.

A longitudinal element (41) extends from the back wall of the cover (4) and branches out into two arms (best seen in FIG. 5). The first arm is a rod-like projection (6) which enters a piece (21) incorporating the blocking sphere (14). The rod-like projection (6) is able to move throughout the piece (21) via a passage (11), when the blocking sphere (14) is in its non-blocking position. The second arm is somewhat longer and forms a sphere-releasing arm (22) having an upwardly extending end portion (23). The piece (21) has a second passage (24) into which the upwardly extending end portion (23) of the sphere-releasing arm (22) can enter, when the cover (4) is in the upper (rest) position. The piece (21) incorporating the blocking sphere (14) is further provided with a loop-like duct consisting of a first channel (25) and the second channel (26). The sphere (14) is able to move along the first channel (25) towards its non-blocking position in response to the inhalation force and along the second channel (26) towards its non-blocking position in response to the gravitational force.

Figure 3:
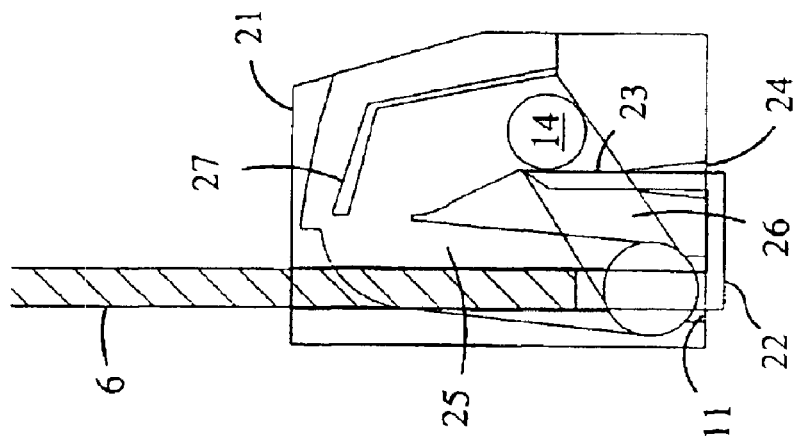
FIG. 3 is a side view of the multiple dosage preventing means of the device of FIG. 1 immediately after inhalation.

FIG. 3 shows the starting situation immediately after a dose has been inhaled. The cover (4) and the projection (6) are in the upper (rest) position urged by the spring (16). The sphere (14) is positioned in its first non-blocking position at the entry of the second channel (26). The sphere is supported in its first non-blocking position by the upwardly extending end portion (23) of the sphere-releasing arm (22).

Figure 4:
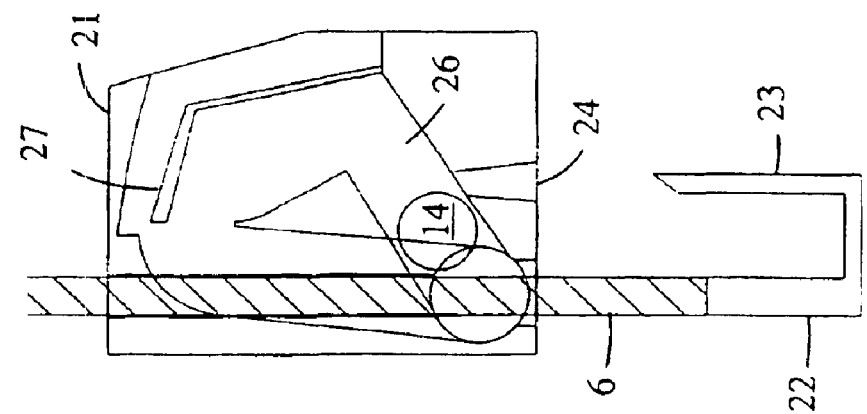
FIG. 4 is a side view of the multiple dosage prevention means of the device when the actuator has been depressed.

FIG. 4 shows the situation when the cover (4) has been pressed down for the actuation of the inhaler. FIG. 5 is a back view of the structure shown FIG. 4. The projection (6) and the sphere-releasing arm (22) are in their lower position, whereby the sphere (14) is no longer supported by the upwardly extending end portion (23) of the sphere-releasing arm (22). As a consequence the gravitational force moves the sphere (14) along the channel (26) to its second non-blocking position, wherein the sphere (14) leans against the projection (6).

Figure 6:
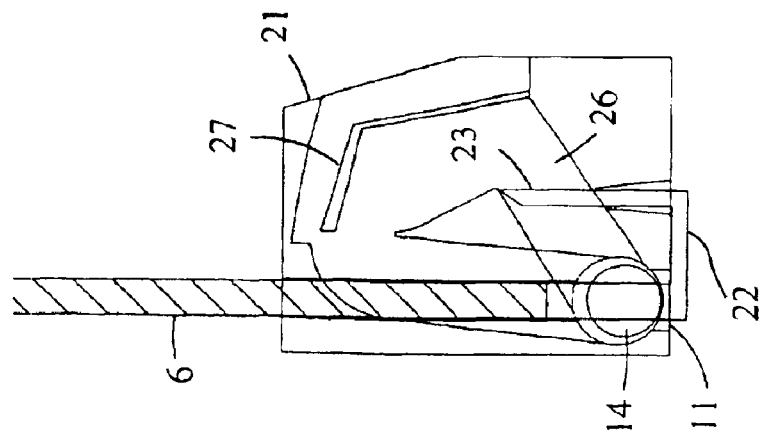
FIG. 6 is a side view of the multiple dosage preventing means of the device when the actuator has been released.

FIG. 6 shows the situation when the depressed cover (4) has been released, whereby the cover (4) returns to its upper (rest) position by the action of the spring (16). At the same time the driving member (18) moves the metering disc (7) clockwise one step, whereby a new metered dose is transferred to the inhalation channel (5), and the inhaler device is ready for the inhalation effort by the user. As the cover (4) is released, the projection (6) is moved upwards. Thereby the sphere (14) is able to continue its movement urged by the gravitational force to its blocking position, wherein the sphere (14) blocks the passage (11). At the same time the upwardly extending end portion (23) of the sphere-releasing arm (22) returns to its initial position and closes the second channel (26). The cover (4) is now locked to its upper (rest)

position, since the sphere (14) prevents the downward movement of the projection (6) in the passage (11). Thereby the rotation of the metering disc (7) is also prevented and multiple dosing is not possible. A flap element (27) prevents the exit of the sphere (14) into the second channel (26) even if the device is turned upside down.

When the user now inhales through the inhaler device, the pressure change in the inhalation channel forces the sphere (14) to rise along the first channel (25), which is in fluid connection with the inhalation channel (5). The flap element (27) is bending slightly in response to the pressure change and allows the sphere (14) to be dropped into its first non-blocking position. After inhalation the flap element (27) prevents the return of the sphere (14) into its blocking position even if the device is turned upside down.

Figure 7:
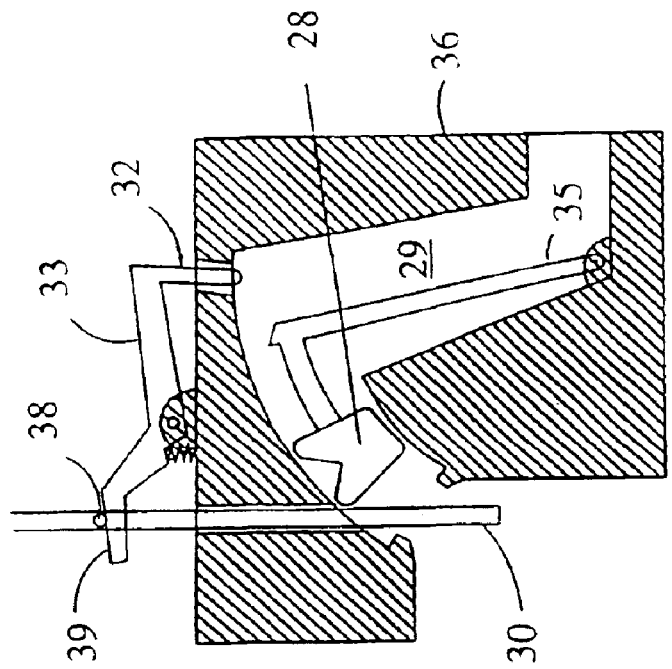
FIG. 7 is a side view of an another embodiment of the multiple dosage preventing means immediately after inhalation.
Figure 8:
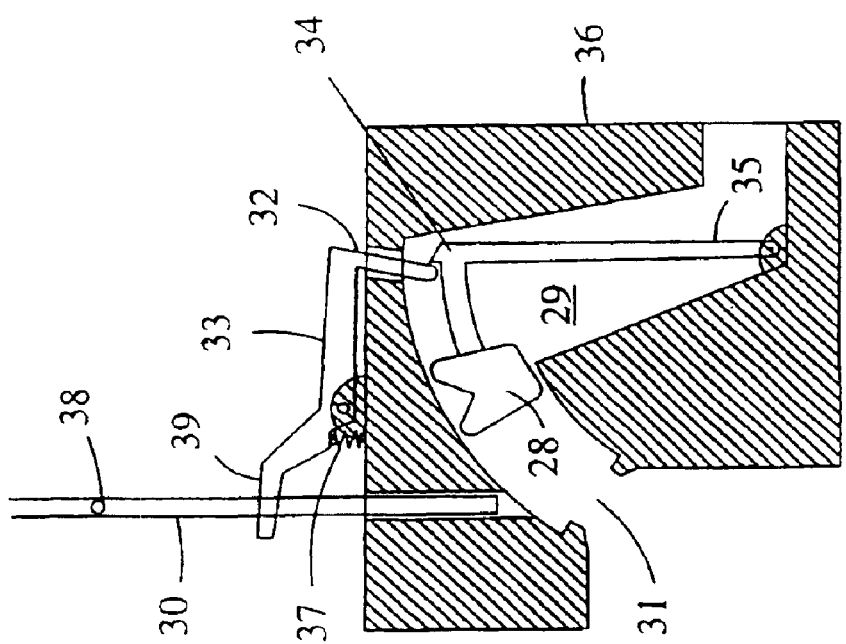
FIG. 8 is a side view of the multiple dosage preventing means of FIG. 7 when the actuator has been depressed.
Figure 9:
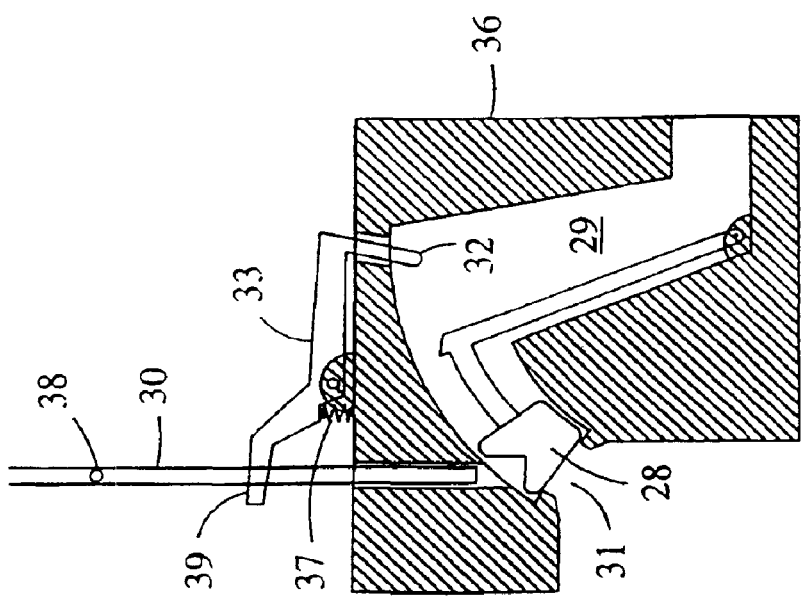
FIG. 9 is a side view of the multiple dosage preventing means of FIG. 7 when the actuator has been released.

A second embodiment of the multiple dosage preventing means is shown in FIGS. 7–9. The blocking element is in the form of a flap (28) pivotally mounted in a channel (29), which is in fluid connection with the inhalation channel. FIG. 7 shows the situation immediately after a dose has been inhaled. The cover (not shown) and the projection (30) extending from the cover are in the upper (rest) position urged by the spring. Again, there is a passage (31) through which the projection (30) is able to move when the cover is depressed. A pivotally mounted flap (28) is maintained in its first non-blocking position by a flap-releasing arm (32) of a rocker (33), wherein the flap-releasing arm (32) of the rocker (33) is engaged with a nose (34) extending from the shaft (35) of the flap (28). The rocker (33) is pivotally mounted on the ceiling of the piece (36) and is biased by a spring (37) to a position where the flap-releasing arm (32) is in its lower position, i.e. the position where it is able to engage with the nose (34).

FIG. 8 shows the situation when the cover (4) has been pressed down for the actuation of the inhaler. The projection (30) has now moved to its lower position, whereby two things have happened. First, a finger (38) extending perpendicularly from the projection (30) has contacted and pressed down the wing (39) of the rocker (33) which wing is opposite to the flap-releasing arm (32). This causes the flap-releasing arm (32) to rise to its upper position, whereby the engagement of the flap-releasing arm (32) with the nose (34) of the shaft (35) is released. As a consequence the gravitational force causes to flap (28) to pivot to its second non-blocking position, where the flap (28) leans against the depressed projection (30).

FIG. 9 shows the situation when the depressed cover (4) has been released, whereby the cover (4) returns to its upper (rest) position by the action of the spring. As the cover (4) is released, the projection (30) is moved upwards. Thereby the flap (28) is able to continue its movement urged by the gravitational force to its blocking position, wherein the flap (28) blocks the passage (31). At the same time the finger (38) of the projection (30) is detached from the wing (39) of the rocker (33). The spring (37) of the rocker (33) urges the rocker (33) back to its initial position, whereby the flap-releasing arm (32) moves again to its lower position. The cover (4) is now locked to its upper (rest) position, since the flap (28) prevents the downward movement of the projection (30) in the passage (31). Thereby the movement of the metering disc (7) is also prevented and multiple dosing is not possible.

Other modifications and variations can be made to the disclosed embodiments without departing from the subject of the invention as defined in the following claims. For example, a counter could be mounted to the inhaler to count the number of pressing of the actuating means. Also the mouthpiece can be equipped with a one-way valve to prevent exhaling through the device. It is considered to be routine for one skilled in the art to make such modifications to the device of the invention.

What is claimed is:

1. A manually actuatable inhaler device allowing actuation before inhalation by the user, comprising a container for powdered medicament;

an inhalation channel through which air can be drawn via a mouthpiece;

a movable metering member for metering a dose of powder in a first position, and for transferring a metered dose of powder into the inhalation channel in a second position;

a depressible actuator for the displacement of the metering member between the first and the second position;

a multiple dosage preventing means for locking the depressible actuator after it has been used such that the actuator is unlocked only upon inhalation comprising a projection communicating with the actuator, a passage in which the projection moves when the actuator is depressed, and a blocking element which, after the device has been actuated, by means of gravitational force moves to a position where it blocks the passage, and which by means of an inhalation force moves to a position where it opens the passage.

2. A device according to claim 1, wherein the blocking element is movably mounted in the inhalation channel or other channel which is in a fluid communication with the inhalation channel.

3. A device according to claim 1, wherein the depressible actuator is biased to return to its rest position after a depressing force is removed.

4. A device according to claim 1, wherein the projection extends from the depressible actuator.

5. A device according to claim 1, wherein the blocking element has a first non-blocking position, into which the blocking element moves after inhaling, a second non-blocking position, into which the blocking element moves when the actuator is again depressed, and a blocking position into which the blocking element moves when the depressible actuator is subsequently released.

6. A device according to claim 5, wherein the blocking element leans against the projection in its second non-blocking position.

7. A device according to claim 1, wherein the element is in the form of a sphere.

8. A device according to claim 1, wherein the element is in the form of a flap.

* * * * *